United States Patent [19]

Safir

[11] 3,951,981

[45] Apr. 20, 1976

[54] SUBSTITUTED BENZODIAZEPINES AND METHOD OF USE

[75] Inventor: Sidney Robert Safir, River Edge, N.J.

[73] Assignee: American Cyanamid Company, Stamford, Conn.

[22] Filed: Feb. 24, 1975

[21] Appl. No.: 552,022

[52] U.S. Cl. .................. 260/268 TR; 260/329 F; 260/293.57; 424/250

[51] Int. Cl.² .................................. C07D 295/12
[58] Field of Search ...... 260/268 TR, 329 F, 293.57

Primary Examiner—Richard J. Gallagher
Assistant Examiner—Jose Tovar
Attorney, Agent, or Firm—Denis A. Polyn

[57] ABSTRACT

10-Substituted amino-4,9-dihydro-4H-thieno[3,4-b]-[1,5]benzodiazepines having neuroleptic and analgesic activity.

8 Claims, No Drawings

SUBSTITUTED BENZODIAZEPINES AND METHOD OF USE

DESCRIPTION OF THE INVENTION

This invention is concerned with compounds of the formula:

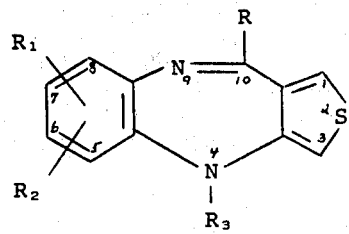

wherein $R_1$ and $R_2$ are selected from the group consisting of hydrogen, lower alkyl, lower alkoxy, halogen, nitro, trifluoromethyl, methylthio, methylsulfonyl and hydroxy; $R_3$ is hydrogen or lower alkyl; R is

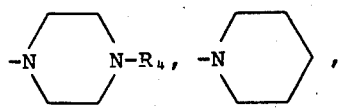

or $-N(CH_2)_nN(R_5)$, wherein $R_4$ is hydrogen, lower alkyl, 2-hydroxyethyl, phenyl or phenylloweralkyl; $n$ is 2 or 3 and $R_5$ is lower alkyl, and acid addition salts thereof. The term lower as defined above is intended to include those wherein the hydrocarbon group contains from 1 to 4 carbon atoms. Halogen is chlorine, bromine, fluorine or iodine.

The compounds of the present invention may be prepared by the following reaction sequence:

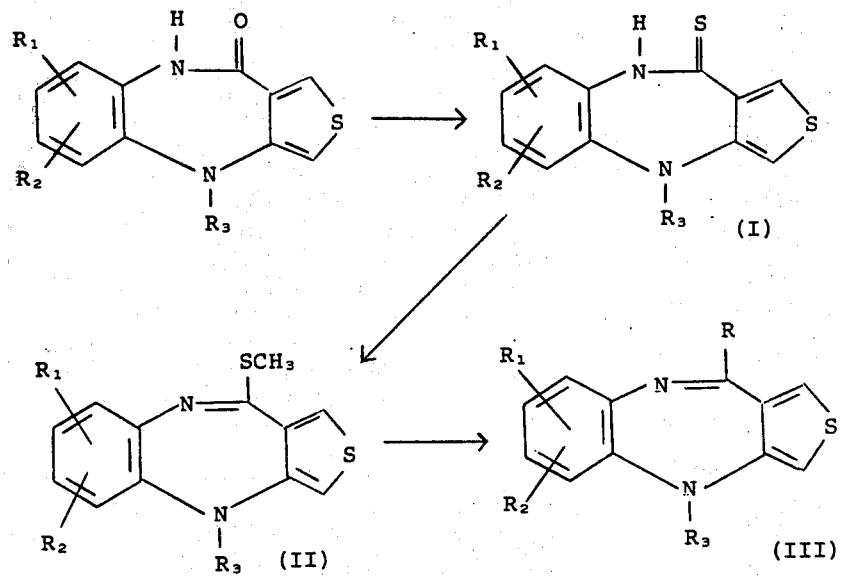

wherein R, $R_1$, $R_2$ and $R_3$ are as defined above.

The starting material, a substituted 4,9-dihydro-10H-thieno[3,4-b][1,5]benzodiazepin-10-thione (I) is prepared from the reaction of the corresponding 4,9-dihydro-10H-thieno[3,4-6][1,5]benzodiazepin-10-one (described in my copending application Ser. No. 552,023 (Case No. 25,618) filed Feb. 24, 1975, and phosphorus pentasulfide in a solvent such as pyridine at reflux. This intermediate (I) is then converted to the correspondingly substituted 10-(methylthio)-4H-thieno[3,4-b][1,5]benzodiazepine (II) by reaction with methyl sulfate and an alkaline base in methanol. The latter reaction is carried out at from 40° to 100°C. for a period of from about ½ hours to 10 hours. The intermediate (II) is the converted to the corresponding 10-substituted amino-4,9-dihydro-4H-thieno[3,4-b][1,5]benzodiazepine (III) by reaction with the appropriate amine at reflux temperature in acid. The temperature of the reaction may vary from 100° to 250°C. depending upon the amine. The reaction is heated from 10 to 120 hours.

Specific compounds included within the scope of this invention are:

10-(4-Methyl-1-piperazinyl)-4H-thieno[3,4-b][1,5]benzodiazepine
7-Chloro-4-methyl-10-(4-methyl-1-piperazinyl)-4H-thieno[3,4-b][1,5]benzodiazepine
6-Chloro-10-(4-methyl-1-piperazinyl)-4H-thieno[3,4-b][1,5]benzodiazepine
7-Chloro-10-(4-methyl-1-piperazinyl)-4H-thieno[3,4-b][1,5]-benzodiazepine
4-Methyl-10-(4-methyl-1-piperazinyl)-4H-thieno[3,4-b][1,5]benzodiazepine
10-Piperidino-4H-thieno[3,4-b][1,5]benzodiazepine
10-(1-Piperazinyl)-4H-thieno[3,4-b][1,5]benzodiazepine
10-[4-(2-Hydroxyethyl)-1-piperazinyl]-4H-thieno[3,4-b][1,5[benzodiazepine
10-(4-Phenyl-1-piperazinyl)-4H-thieno[3,4-b][1,5]benzodiazepine
10-(4-Benzyl-1-piperazinyl)-4H-thieno[3,4-b][1,5]benzodiazepine
7-chloro-10-[4-(2-hydroxyethyl)-1-piperazinyl]-4H-thieno[3,4-b][1,5]benzodiazepine
4-Methyl-10-(1-piperazinyl)-4H-thieno[3,4-b][1,5]benzodiazepine
10-[4-(2-Dimethylaminoethyl)-1-piperazinyl]-4H-thieno[3,4-b][1,5]benzodiazepine 5-Fluoro-10-(4-methyl-1-piperazinyl)-4H-thieno[3,4-b][1,5]benzodiazepine 6-Trifluoromethyl-10-(1-piperazinyl)-4H-thieno[3,4-b][1,5]benzodiazepine 6-Fluoro-4-methyl-10-(4-methyl-1-piperazinyl)-4H-thieno[3,4-b][1,5]benzodiazepine 7-Methoxy-10-(4-methyl-1-piperazinyl)-4H-thieno[3,4-b][1,5]benzodiazepine 6,7-Dichloro-10-(4-methyl-1-piperazinyl)-4H-thieno[3,4-b][1,5]benzodiazepine 5-Methoxy-10-(1-piperazinyl)-4H-thieno[3,4-b][1,5]benzodiazepine 6,7-Dimethyl-10-[4-(2-hydroxyethyl)-1-piperazinyl]-4H-thieno[3,4-b][1,5]benzpdiazepine 6,7-Dimethoxy-10-(4-methyl-1-piperazinyl)-4H-thieno[3,4-b][1,5]benzodiazepine 8-Chloro-10-(1-piperazinyl)-4H-thieno[3,4-b][1,5]benzodiazepine 4-Ethyl-10-(4-methyl-1-piperazinyl)-4H-thieno[3,4-b][1,5]benzodiazepine 7-Chloro-4-propyl-10-(4-methyl-1-piperazinyl)-4H-thieno[3,4-b][1,5]benzodiazepine 7-Chloro-4-methyl-10-(1-piperazinyl-4H-thieno[3,4-b][1,5]benzodiazepine 7-Chloro-10-(1-piperazinyl)-4H-thieno[3,4-b][1,5]benzodiazepine 5-Chloro-10-(4-methyl-1-piperazinyl)-4H-thieno[3,4-b][1,5]benzodiazepine 7-Hydroxy-10-(4-methyl-1-piperazinyl)-4H-thieno[3,4-b][1,5]benzodiazepine 6-Hydroxy-10-(4-methyl-1-piperazinyl)-4H-thieno[3,4-b][1,5]benzodiazepine 10-[4-(3-Dimethylaminopropyl)-1-piperazinyl]-4H-thieno[3,4-b][1,5]benzodiazepine 7-Methylsulfonyl-10-(4-methyl-1-piperazinyl)-4H-thieno[3,4-b][1,5]benzodiazepine 10-(1-Piperazinyl)-4-ethyl-4H-thieno[3,4-b][1,5]benzodiazepine 4-Ethyl-10-[4-(2-hydroxyethyl)-1-piperazinyl]-4H-thieno[3,4-b][1,5]benzodiazepine 7-Nitro-10-(4-methyl-1-piperazinyl)-4H-thieno[3,4-b][1,5]benzodiazepine 6-Methylthio-10-(4-methyl-1-piperazinyl-4H-thieno[3,4-b][1,5]benzodiazepine The compounds of the present invention are active analgesics when measured by the "writhing syndrome" test for analgesic activity as described by Siegmund, et al., Proc. Soc. Exp. Bio, and Med., 95, 729 (1957), with modifications. This method is based upon the reduction of the number of writhes following the intraperitoneal injection of one mg./kg. of body weight of phenyl p-quinone in male Swiss albino mice weighing 15–25 g. The syndrome is characterized by intermittent contractions of the abdomen, twisting abd turning of the trunk, and extension of the hind legs beginning 3 to 5 minutes after injection of the phenyl p-quinone. The test compounds are administered orally at the indicated dose to groups of 2 mice each, 30 minutes before injection of the phenyl p-quinone. The total number of writhes exhibited by each group of mice is recorded for a 3 minute period commencing 15 minutes after injection of the phenyl p-quinone. A compound is considered active if it reduces the total number of writhes in 2 test mice from a control value of approximately 30 per pair to a value of 18 or less. Table I summarizes the results of this test on representative compounds of this invention.

Table I

| Compound | Dose (mg/Kg) | No. of Writhes Per Pair |
|---|---|---|
| 10-(4-Methyl-1-piperazinyl)-4H-thieno-[3,4-b][1,5]benzodiazepine | 6.25 | 4, 2 |
| 4-Methyl-10-(4-methyl-1-piperazinyl)-4H-thieno[3,4-b][1,5]benzodiazepine | 50 | 0, 0 |
| 7-Chloro-10-(4-methyl-1-piperazinyl)-4H-thieno[3,4-b][1,5]benzodiazepine diperchlorate | 1.6 | 1, 2 |
| 6-Chloro-10-(4-methyl-1-piperazinyl)-4H-thieno[3,4-b][1,5]benzodiazepine | 6.25 | 7, 6 |
| 7-Chloro-4-methyl-10-(4-methyl-1-piperazinyl)-4H-thieno[3,4-b][1,5]benzodiazepine diperchlorate | 1.6 | 6, 2 |

The compounds of this invention are useful for the relief of pain and inflammation in warm-blooded animals. To determine analgesic activity, a modification of the method of Randall and Selitto [Arch. Int, Pharmacodyn., 111, 409 (1957)] is used. This test measures the pain threshold of rats whose paws are made sensitive to pressure by the injection of 0.1 ml. of a 20% aqueous suspension of brewers yeast into the plantar surface of the left hind paw. Constantly increasing force (16 g/second) is applied to the swollen paw using an Analgesy Meter, Ugo Basile. The pressure is cut off at 250 g. of force where there is no response (sudden struggle or vocalization). Control rats treated with starch vehicle respond to a pressure of about 30 g. Pressure-pain thresholds are always recorded 2 hours after administration of Brewers' yeast. Test compounds are administered at the same time as the yeast, at an oral dose of 200 mg/Kg. Ratios of treated (T)/control(C) reaction thresholds are calculated as estimates of analgesic efficacy (degree of analgesia obtainable). Test compounds are accepted as active when they produce a 100% elevation of pain (T/C $\geq$ 1.37). The results of this test on representative compounds of the present invention appear in Table II.

Table II

| Compound | Ratio T/C |
|---|---|
| 10-(4-Methyl-1-piperazinyl)-4H-thieno[3,4-b][1,5]benzodiazepine | 1.57 |
| 7-Chloro-4-methyl-10-(4-methyl-1-piperazinyl)-4H-thieno[3,4-b]-[1,5]benzodiazepine diperchlorate | 1.55 |

The compounds of the present invention are physiologically active on the central nervous system and show high activity as anti-psychotic or neuroleptic agents. A useful test for anti-psychotic activity consists of measuring the reduction of spontaneous motor activity in animals.

Groups of 4 rats are treated orally with the test compound dissolved or suspended in starch vehicle at the maximum tolerated dose. At the estimated time of peak effect, the animals are placed singly into an Animax Activity Counter and the activity of each rat is recorded over a 5 minute period. The activity counts are compared to historical or parallel control valves to determine significant increased or decreased locomotor activity.

The compound is considered an active depressant if the counts are 50% or less of control values.

Median effective doses (MDD$_{50}$) (doses which decrease locomotor activity by 50%) are determined, in groups of 6 rats, for those compounds deemed active, by a method of least-squares [D.F. Finney, Statistical Methods in Biological Assay, Second Edition, Hofner Publishing Co., New York, 456–457 (1964)]. The effective does that causes a 50% reduction in motor activity (MDD$_{50}$), expressed in mg/Kg of body weight, of some typical compounds of this invention is set forth in Table III.

Table III

| Compound | MDD$_{50}$ (mg/Kg) |
| --- | --- |
| 10-(4-Methyl-1-piperazinyl)-4H-thieno[3,4-b][1,5]benzodiazepine | 6.1 |
| 6-Chloro-10-(4-methyl-1-piperazinyl)-4H-thieno[3,4-b][1,5]benzodiazepine | 7.7 |
| 7-Chloro-10-(4-methyl-1-piperazinyl)-4H-thieno[3,4-b][1,5]benzodiazepine diperchlorate | 20 |
| 7-Chloro-4-methyl-10-(4-methyl-1-piperazinyl)-4H-thieno[3,4-b]-[1,5]benzodiazepine diperchlorate | 25 |
| 4-Methyl-10-(4-methyl-1-piperazinyl)-4H-thieno[3,4-b][1,5]benzodiazepine | 12 |

The compounds of the present invention are physiologically active on the central nervous system and show high activity as anti-psychotic or neuroleptic agents. A useful test for anti-psychotic activity consists of measuring ptosis in animals.

Ptosis is defined as closure of the palpebral aperture (eyelid) greater than 70%. The compounds to be tested were administered orally to groups of 10 rats each. Periodically after treatment the rats were gently placed on the cage top and examined for 90 seconds for signs of ptosis. This manipulation eliminates spontaneous ptosis. The ras were then dropped from a height of about 18 inches (exteroceptive stimulation) onto the cage top to test for reversibility of ptosis. Reversible ptosis is defined as less than 70% closure of the palpebral aperture for longer than 1 minute after the exteroceptive stimulation and is indicative of neuroleptic activity of the drug administered. This test has been described by Tedeschi, D. H., "Criteria for the Selection of Pharmacological Test Procedures Useful in the Evaluation of Neuroleptic Drugs", *Proceedings of the VI International Congress of the Collegium Internationale Neuropsychopharmacologicum*, pp. 145–153, (1968). The results of this test on representative compounds of the present invention appear in Table IV, wherein the dose (ED$_{50}$) estimated to create reversible ptosis in 50% of the animals is given.

Table IV

| Compound | ED$_{50}$ (mg/Kg) |
| --- | --- |
| 10-(4-Methyl-1-piperazinyl)-4H-thieno[3,4-b][1,5]benzodiazepine | 13 |
| 7-Chloro-10-(4-methyl-1-piperazinyl)-4H-thieno[3,4-b][1,5[benzodiazepine diperchlorate | 10 |
| 6-Chloro-10-(4-methyl-1-piperazinyl)-4H-thieno[3,4-b][1,5]benzodiazepine | 17 |

The compounds of the present invention exhibit anti-psychotic activity when measured by the Discrete Trial Conditioned Avoidance Test.

In this test the compounds are administered orally to male Long-Evans rats in a universal starch vehicle. The rats have been pre-conditioned to make a 70% avoidance response.

The rats are placed in individual cages and a warning tone is sounded every 20 seconds. Each rat has the opportunity to press a bar which, if done within 5 seconds, prevents an electric shock through the grid floor of the cage and is termed an avoidance response.

Each rat is given 50 trials and a score of avoidance responses is kept. The drug is administered at various dose levels. Drugs exhibiting anti-psychotic activity are known to block this avoidance response.

The effective median dose (ED$_{50}$) which reduces avoidance response by 50% as compared to controls is estimated. The results of such a test are recorded in Table V.

Table V

| Compound | ED$_{50}$ (mg/Kg) |
| --- | --- |
| 10-(4-Methyl-1-piperazinyl)-4H-thieno[3,4-b][1,5]benzodiazepine | 7 |
| 4-Methyl-10-(4-methyl-1-piperazinyl)-4H-thieno[3,4-b][1,5]benzodiazepine | 17 |
| Chlorpromazine | 9 |

The active components of this invention can be used in compositions such as tablets; the principal active ingredient is mixed with conventional tableting ingredients such as corn starch, lactose, sucrose, sorbitol, talc, stearic acid, magnesium stearate, dicalcium phosphate, gums or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating.

The liquid forms in which the novel compositions of the present invention may be incorporated for administration include suitably flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subject, each unit containing a predetermined quantity of active component calculated to produce the desired therapeutic effect in association with the required pharmaceutical diluent, carrier or vehicle. The dosage may vary from 1 to 70 mg. per kg. of warm-blooded animal per day preferably in multiple doses. The daily dosage requirement may be form 50 to 2000 mg. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

EXAMPLE 1

Preparation of 4,9-Dihydro-10H-thieno[3,4-b][1,5]benzodiazepine-10-thione

A mixture of 0.76 g. of 4,9-dihydro-10H-thieno[3,4-b][1,5]benzodiazepin-10-one and 1.0 g. of phosphorus pentasulfide in 10 ml. of dry pyridine is stirred and heated under reflux for 4 hours. The reaction mixture is concentrated to dryness and the oily residue is stirred for 18 hours with 25–30 ml. of 1N sodium carbonate solution (pH 7–7.2). The solid thus obtained is collected, washed with water and recrystallized from methanol to give orange crystals, m.p. 210°–212°C.

In a similar fashion 7-fluoro-4,9-dihydro-10H-thieno[3,4-b][1,5]benzodiazepin-10-one is treated with phosphorus pentasulfide to give 7-fluoro-4,9-dihydro-10H-thieno[3,4-b][1,5]-benzodiazepine-10-thione.

Employing the same general procedure the following starting materials produce the listed products:

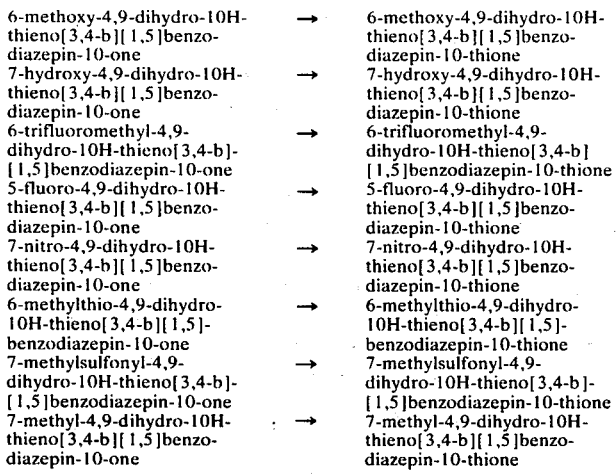

EXAMPLE 2

Preparation of 10-(Methylthio)-4H-thieno[3,4-b][1,5]benzodiazepine

To a stirred suspension of 1.3 g. of 4,9-dihydro-10H-thieno[3,4-b][1,5]benzodiazepin-10-thione in 15 ml. of dioxane is added simultaneously at <40°C., a solution of 1.9 g. of potassium hydroxide in 10 ml. of methanol and 2.2 g. of methyl sulfate. After addition is complete, stirring is continued for 1.5 hours. The mixture is diluted with methanol and filtered. The filtrate is concentrated to about 20 ml., diluted with water and filtered. The sticky precipitate is dissolved in chloroform; the chloroform solution is dried and concentrated to give a solid, which is recrystallized from methanol-water to give deep yellow crystals, m.p. 128.5°–130°C.

In a similar manner 7-fluoro-4,9-dihydro-10H-thieno[3,4-b][1,5]benzodiazepin-10-thione is reacted with potassium hydroxide and methyl sulfate to give 7-fluoro-10-(methylthio)-4H-thieno[3,4-b][1,5]benzodiazepine.

Employing the same general procedure the following starting materials produce the listed products:

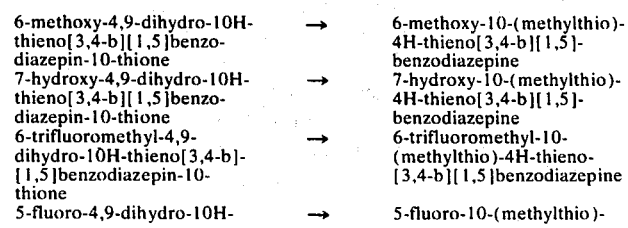

| | -continued | |
|---|---|---|
| thieno[3,4-b][1,5]benzo-diazepin-10-thione | | 4H-thieno[3,4-b][1,5]-benzodiazepine |
| 7-nitro-4,9-dihydro-10H-thieno[3,4-b][1,5]benzo-diazepin-10-thione | → | 7-nitro-10-(methylthio)-4H-thieno[3,4-b][1,5]-benzodiazepine |
| 6-methylthio-4,9-dihydro-10H-thieno[3,4-b][1,5]-benzodiazepin-10-thione | → | 6-methylthio-10-(methyl-thio)-4H-thieno[3,4-b]-[1,5]benzodiazepine |
| 7-methylsulfonyl-4,9-di-hydro-10H-thieno[3,4-b]-[1,5]-benzodiazepin-10-thione | → | 7-methylsulfonyl-10-(methylthio)-4H-thieno-[3,4-b][1,5]benzodiazepine |
| 7-methyl-4,9-dihydro-10H-thieno[3,4-b][1,5]benzo-diazepin-10-thione | → | 7-methyl-10-(methylthio)-4H-thieno[3,4-b][1,5]-benzodiazepine |

EXAMPLE 3

Preparation of
10-(4-Methyl-1-piperazinyl)-4H-thieno[3,4-b][1,5]benzodiazepine

A solution of 1.0 g. of 10-(methylthio)-4H-thieno[3,4-b][1,5]benzodiazepine in 5 ml. of N-methylpiperazine is treated with 2–3 drops of glacial acetic acid and heated under reflux for 4 days. The solution is concentrated to dryness and the residue is warmed with dilute acetic acid. The acidic solution is filtered, cooled and made alkaline with concentrated ammonium hydroxide. The precipitate is collected, washed with water and recrystallized fom acetone-petroleum ether (30°–60°C.) to give yellow crystals, m.p. 197.5°–199°C.

In a similar manner 7-fluoro-10-(methylthio)-4H-thieno[3,4-b] [1,5]benzodiazepine is reacted with N-methylpiperazine to give 7-fluoro-10-(4-methyl-1-piperazinyl)-4H-thieno[3,4-b] [1,5]benzodiazepine and 7-methoxy-10-(methylthio)-4H-thieno[3,4-b] [1,5]benzodiazepine gives 7-methoxy-10-(4-methyl-1-piperazinyl)-4-H-thieno[3,4-b] [1,5]benzodiazepine.

EXAMPLE 4

Preparation of 10-(1-Piperazinyl)-4H-thieno[3,4-b] [1,5]benzodiazepine

A bomb charged with 2.5 g. of 10-(methylthio)-4H-thieno[3,4-b] [1,5]benzodiazepine, 8.6 g. of piperazine, and three drops of acetic acid is placed in an oil bath and heated at 155°–160°C. for 4 days. The bomb is then cooled and the contents are dissolved in 2N acetic acid. The solution is filtered and the filtrate is made alkaline with ammonium hydroxide and extracted with chloroform. The extracts are dried, filtered and evaporated to give a yellow solid. Recrystallization from ethanol gives the product as light tan crystals which melt at 228°–231°C. (dec.).

EXAMPLE 5

Preparation of 10-(Piperidino)-4H-thieno[3,4-b] [1,5]benzodiazepine

A solution of 0.7 g. of 10-(methylthio)-4H-thieno[3,4-b] [1,5]benzodiazepine in 5 ml. of piperidine is treated with a drop of glacial acetic acid and heated under reflux for 4 days. Excess piperidine is removed under reduce pressure and the oily residue is warmed with dilute acetic acid and filtered. The filtrate is cooled and made alkaline with concentrated ammonium hydroxide to give a yellow solid. Recrystallization from acetone-petroleum ether (30°–60°C.) gives yellow crystals, m.p. 157°–159°C.

EXAMPLE 6

Preparation of
4,9-Dihydro-4-methyl-10-H-thieno[3,4-b][1,5]benzodiazepin-10-thione A mixture of 0.4 g. of 4,9-dihydro-4-methyl-10H-thieno[3,4-b] [1,5]benzodiazepin-10-one and 0.5 g. of phosphorus pentasulfide in 5 ml. of dry pyridine is stirred and heated under reflux for 4 hours. The reaction mixture is concentrated to dryness and the residue is stirred with 10 ml. of 1N sodium carbonate solution for 18 hours. The precipitate is collected, washed with water and recrystallized from methanol to give gold crystals, m.p. 203°–204°C.

EXAMPLE 7

Preparation of
4-Methyl-10-(methylthio)-4H-thieno[3,4-b][1,5]benzodiazepine

To a stirred suspension of 0.7 g. of 4,9-dihydro-4-methyl-10H-thieno[3,4-b] [1,5]benzodiazepin-10-thione in 10 ml. of dioxane is added dropwise and simultaneously at 30°–40°C., a solution of 0.95 g. of potassium hydroxide in 10 ml. of methanol and 0.8 ml. of methyl sulfate. After addition is complete, the mixture is stirred for 3 hours, diluted with methanol and filtered. The filtrate is concentrated to about 20 ml., diluted with water and extracted with chloroform. The chloroform solution is concentrated to give a solid, which is recrystallized from methanol-water to give orgnae crystals, m.p. 113°–115°C.

EXAMPLE 8

Preparation of
4-Methyl-10-(4-methyl-1-piperazinyl)-4H-thieno[3,4-b][1,5]benzodiazepine A solution of 1.2 g. of 4-methyl-10-(methylthio)-4H-thieno[3,4-b] [1,5]benzodiazepine in 6 ml. of N-methylpiperazine is treated with 2–3 drops of glacial acetic acid and heated under reflux for 4 days. The solution is concentrated to dryness and the residue is warmed with dilute acetic acid. The acidic solution is filtered, cooled, and made alkaline with concentrated ammonium hydroxide solution. The precipitate is collected, washed with water and dissolved in chloroform. The chloroform solution is dried and concentrated to an oil, which slowly crystallizes. Recrystallization from ethanol gives yellow crystals, m.p. 83°–85°C.

EXAMPLE 9

Preparation of a mixture of
6-Chloro-1,3,4,9-tetrahydro-10H-thieno[3,4-b][1,5]benzodiazepin-10-one and
7-Chloro-1,3,4,9-tetrahydro-10H-thieno[3,4-b][1,5]benzodiazepin-10-one A solution of 0.4 g. of methyl tetrahydro-4-oxo-3-thiophenecarboxylate and 0.36 g. of 4-chloro-o-phenylenediamine in 20 ml. of toluene is heated under reflux for 3 hours, cooled and filtered. The solid obtained is recrystallized from dimethylformamide to give a yellow solid, m.p. 233°–235°C. (dec.).

EXAMPLE 10

Preparation of
6-Chloro-4,9-dihydro-10H-thieno[3,4-b][1,5]benzodiazepin-10-one and
7-Chloro-4,9-dihydro-10H-thieno[3,4-b][1,5]benzodiazepin-10-one To a suspension of 1.5 g. of the mixture of 6-chloro-1,3,4,9-tetrahydro-10H-thieno[3,4-b] [1,5]benzodiazepin-10-one and 7-chloro-1,3,4,9-tetrahydro-10H-thieno[3,4-b] [1,5]benzodiazepin-10-one (prepared as described in Example 9) in 15 ml. of dry pyridine is added, in portions, 0.8 g. of N-chlorosuccinimide. The resulting solution is heated on a steam bath for 15–20 minutes, cooled and diluted with water. The precipitate is collected and recrystallized from methanol to give deep gold crystals, m.p. 279°–281°C., with are pure 6-chloro-4,9-dihydro-10H-thieno[3,4-b] [1,5]benzodiazepin-10-one. The methanol filtrate is diluted with water to give a yellow solid, m.p. 197°–198°C. which is pure 7-chloro-4,9-dihydro-10H-thieno[3,4-b] 1,5]benzodiazepin-10-one.

EXAMPLE 11

Preparation of
7-Chloro-4,9-dihydro-10H-thieno[3,4-b][1,5]benzodiazepin-10-thione A mixture of 0.88 g. of 7-chloro-4,9-dihydro-10H-thieno[3,4-b][1,5]benzodiazepin-10-one and 1.0 g. of phosphorus pentasulfide in 10 ml. of dry pyridine is stirred and heated under reflux for 4 hours. The mixture is concentrated to dryness and the residue is stirred in 20 ml. of 1N sodium carbonate solution (pH 7–7.2) for 18 hours. The precipitate is collected, washed with water and recrystallized from methanol-water to give a deep yellow solid, m.p. 197°–198.5°C. (dec.).

EXAMPLE 12

Preparation of
7-Chloro-10-(methylthio)-4H-thieno[3,4-b][1,5]benzodiazepine

To a stirred suspension of 0.8 g. of 7-chloro-4,9-dihydro-10H-thieno[3,4-b] [1,5]benzodiazepine-10-thione in 10 ml of dioxane is added dropwise and simultaneously at 30°–40°C., a solution of 0.95 g. of potassium hydroxide in 10 ml. of methanol and 0.8 g. of methyl sulfate. After addition is complete, the reaction mixture is stirred for 3 hours, diluted with methanol and filtered. The filtrate is concentrated to 20 ml., diluted with water and extracted with chloroform. The chloroform solution is concentrated under reduced pressure to give a solid, which is recrystallized from methanol-water to give yellow crystals, m.p. 111°–113°C.

EXAMPLE 13

Preparation of
7-Chloro-10-(4-methyl-1-piperazinyl)-4H-thieno[3,4-b] [1,5]benzodiazepine diperchlorate A solution of 0.9 g. of 7-chloro-10-(methylthio)-4H-thieno[3,4-b] [1,5] benzodiazepine in 4.5 ml. of N-methylpiperazine is treated with 2–3 drops of glacial acetic acid and heated under reflux for 4 days. The solution is concentrated to dryness and the residue is warmed with dilute acetic acid. The acidic solution is filtered, cooled and made alkaline with concentrated ammonium hydroxide. The sticky precipitate is collected and dissolved in chloroform. The dried chloroform solution is concentrated under reduced pressure to give 7-chloro-10-(4-methyl-1-piperazinyl)-4H-thieno[3,4-b] [1,5]benzodiazepine as an oil. An ethanolic solution of the oil is treated with 70% perchloric acid and diluted with water. The precipitate is recrystallized from methanol to give yellow crystals, m.p. 268°–270°C. (dec.).

EXAMPLE 14

Preparation of
6-Chloro-4,9-dihydro-10H-thieno[3,4-b][1,5]benzodiazepine-10-thione A mixture of 0.88 g. of 6-chloro-4,9-dihydro-10H-thieno[3,4-b] [1,5]benzodiazepin-10-one and 1.0 g. of phosphorus pentasulfide in 10 ml. of dry pyridine is stirred and heated under reflux for 4 hours. The reaction mixture is concentrated to dryness and the residue is stirred with 20 ml. of 1N sodium carbonate solution (pH 7–7.2) for 18 hours. The precipitate is collected, washed with water and recrystallized from methanol to give an organic solid, m.p. 235°–237°C. (dec.).

EXAMPLE 15

Preparation of
6-Chloro-10-(methylthio)-4H-thieno[3,4-b][1,5]benzodiazepine

To a stirred suspension of 0.7 g. of 6-chloro-4,9-dihydro-10H-thieno[3,4-b] [1,5]benzodiazepin-10-thione in 10 ml. of dioxane is added dropwise and simultaneously at 30°–40°C., a solution of 0.95 g. of potassium hydroxide in 10 ml. of methanol and 0.8 g. of methylsulfate. After addition is complete, the mixture is stirred for 3 hours, diluted with methanol and filtered. The filtrate is concentrated to 20 ml. and diluted with water. The precipitate is collected, washed with water and recrystallized from methanol-water to give yellow crystals, m.p. 152°–154°C.

EXAMPLE 16

Preparation of
6-Chloro-10-(4-methyl-1-piperazinyl)-4H-thieno[3,4-b] [1,5]benzodiazepine A solution of 0.7 g. of 6-chloro-10-(methylthio)-4H-thieno[3,4-b] [1,5]benzodiazepine in 3.5 ml. of N-methylpiperazine is treated with 1–2 drops of glacial acetic acid and heated undr reflux for 4 days. The solution is concentrated to dryness and the residue is warmed with dilute acetic acid. The acidic solution is filtered, cooled, and made alkaline with concentrated ammonium hydroxide. The precipitate is collected, washed with water and recrystallized from acetone-petroleum ether (30°–60°C.) to give yellow crystals, m.p. 148°–149°C. (dec.).

EXAMPLE 17

Preparation of a mixture of
7-Chloro-1,3,4,9-tetrahydro-4-methyl-10H-thieno[3,4-b] [1,5]benzodiazepin-10-one and
6-Chloro-1,3,4,9-tetrahydro-9-methyl-10H-thieno[3,4-b][1,5]benzodiazepin-10-one A solution of 2.8 g. of methyl tetrahydro-4-oxo-3-thiophenecarboxylate and 4.0 g. of 5-chloro-2-methylaminoaniline in 200 ml of toluene is heated under reflux for 3 hours, during which 100 ml. of distillate is collected. The solution is cooled and the solid is collected and recrystallized from ethylacetate to give a yellow solid, m.p. 233°–235°C. (dec.).

EXAMPLE 18

Preparation of
7-Chloro-4-methyl-4,9-dihydro-10H-thieno[3,4-b][1,5]benzodiazepin 10-one To a suspension of 0.53g. of the mixture of 7-chloro-4-methyl-1,3,4,9-tetrahydro-10H-thieno[3,4-b] [1,5]benzodiazepin-10-one and 6-chloro-9-methyl-1,3,4,9-tetrahydro-10H-thieno[3,4-b] [1,5]benzodiazepin-10-one (prepared as described in Example 17) in 5 ml. of dry pyridine is added, in portions, 0.27 g. of N-chlorosuccinimide. The resulting solution is heated on a steam bath for 15–20 minutes, cooled, diluted with water and filtered. The solid is recrystallized from methanol to give a yellow solid which consists of the single isomer of the title, m.p. 244°–246°C. (dec.).

EXAMPLE 19

Preparation of
7-Chloro-4-methyl-4,9-dihydro-10H-thieno[3,4-b][1,5]benzodiazepin-10-thione A mixture of 0.5 g. of 7-chloro-4-methyl-4,9-dihydro-10H-thieno[3,4-b] [1,5]benzodiazepin-10-one and 0.5 g. of phosphorus pentasulfide in 5 ml. of dry pyridine is stirred and heated under reflux for 4 hours. The mixture is concentrated to dryness and is stirred with 10 ml. of 1N sodium carbonate solution for 18 hours. The precipitate is collected, washed with water and recrystallized from methanol to give a yellow solid, m.p. 238°–240°C.

EXAMPLE 20

Preparation of
7-Chloro-4-methyl-10-(methylthio)-4H-thieno[3,4-b] [1,5]benzodiazepine To a stirred suspension of 1.1 g. of 7-chloro-4-methyl-4,9-dihydro-10H-thieno[3,4-b] [1,5]benzodiazepin-10-thione in 15 ml. of dioxane is added dropwise and simultaneously at 30°–40°C., a solution of 1.3 g. of potassium hydroxide in 15 ml. of methanol and 1.1 g. of methyl sulfate. After addition is complete, the mixture is stirred for 3 hours, diluted with methanol and filtered. The filtrate is concentrated to 20 ml., diluted with water and the precipitate is collected. Recrystallization from methanol-water gives deep yellow crystals, m.p. 156°–158°C.

EXAMPLE 21

Preparation of
7-Chloro-4-methyl-10-(4-methyl-1-piperazinyl)-4H-thieno[3,4-b] [1,5benzodiazepine diperchlorate A solution of 0.7 g. of 7-chloro-4-methyl-10-(methylthio)-4H-thieno[3,4-b] [1,5]benzodiazepine in 3.5 ml. of N-methylpiperazine is treated with 1–2 drops of glacial acetic acid and heated under reflux for 4 days. The solution is concentrated to dryness and the residue is warmed with dilute acetic acid. The acidic solution is filtered, cooled and made alkaline with concentrated ammonium hydroxide. The sticky precipitate is collected and dissolved in chloroform. The dried chloroform solution is concentrated under reduced pressure to give an oil. An ethanolic solution of the oil is treated with 70% perchloric acid and is diluted with water. The precipitate is collected and recrystallized from ethanol to give a white solid, m.p. 212°–215°C. (dec.).

EXAMPLE 22

Preparation of
7-Methylthio-10-[4-(2-hydroxyethyl)-1-piperazinyl]-4H-thieno[3,4-b] [1,5]benzodiazepine A solution of 7,10-bis(methylthio)-4H-thieno-[3,4-b][1,5]benzodiazepine in excess N-(2-hydroxyethyl)-piperazine and glacial acetic acid is heated at 140°–160°C. for 2 days. The solution is poured into water and the product is collected.

EXAMPLE 23

Preparation of
6-Nitro-10-(4-benzyl-1-piperazinyl)-4H-thieno[3,4-b] [1,5]benzodiazepine A solution of 6-nitro 10-(methylthio)-4H-thieno [3,4-b] [1,5]benzodiazepine in excess N-benzylpiperazine and glacial acetic acid is heated at 140°–160°C. for 2 days. The solution is poured into water and the product is collected.

EXAMPLE 24

Preparation of
7-Hydroxy-10-(4-phenyl-1-piperazinyl)-4H-thieno[3,4-b] [1,5]benzodiazepine A solution of 7-hydroxy-10-(methylthio)-4H-thieno[3,4-b][1,5]benzodiazepine in excess N-phenylpiperazine and glacial acetic acid is heated at 140°–160°C. for 2 days. The solution is poured into water and the product is collected.

EXAMPLE 25

Preparation of
7-Trifluoromethyl-10-[4-(2-dimethylaminoethyl)-1-piperazinyl]-4H-thieno[3,4-b] [1,5]benzodiazepine A solution of 7-trifluoromethyl-10-(methylthio)-4H-thieno[3,4-b][1,5]benzodiazepine in excess 2-dimethylaminoethylamine and glacial acetic acid is heated at 140°–160°C. for 2 days. The solution is poured into water and the product is collected.

EXAMPLE 26

Preparation of
6-Methylsulfonyl-10-(1-piperazinyl)-4H-thieno[3,4-b][1,5-benzodiazepine A solution of 6-methylsulfonyl-10-(methylthio)-4H-thieno[3,4-b][1,5]benzodiazepine in excess piperazine and glacial acetic acid is heated in a bomb at 150°C. for 2 days. The solution is poured into water and the product is collected.

EXAMPLE 27

Preparation of
6-Methoxy-10-(4-methyl-1-piperazinyl)-4H-thieno[3,4-b][1,5]benzodiazepine A solution of 6-methoxy-10-(methylthio)-4H-thieno[3,4-b][1,5]benzodiazepine in excess N-methylpiperazine and glacial acetic acid is heated at reflux for 2 days. The solution is poured into water and the product is collected.

EXAMPLE 28

Preparation of
7-Methyl-10-(4-methyl-1-piperazinyl)-4H-thieno[3,4-b][1,5]benzodiazepine A solution of 7-methyl-10-(methylthio)-4H-thieno[3,4-b][1,5]benzodiazepine in excess N-methylpiperazine and glacial acetic acid is heated at reflux for 2 days. The solution is poured into water and the product is collected.

I claim:

1. A compound selected from those of the formula:

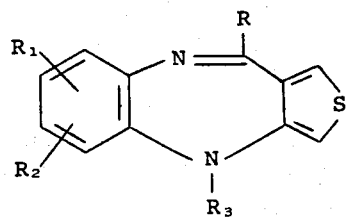

wherein $R_1$ and $R_2$ are selected from the group consisting of hydrogen, lower alkyl, lower alkoxy, halogen, nitro, trifluoromethyl, methylthio, methylsulfonyl and hydroxy; $R_3$ is selected from the group consisting of hydrogen and lower alkyl; R is selected from the group consisting

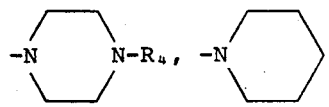

and $-N(CH_2)_nN(R_5)_2$, wherein $R_4$ is selected from the group consisting of hydrogen, lower alkyl, 2-hydroxyethyl, phenyl and phenylloweralkyl, $n$ is 2 or 3 and $R_5$ is lower alkyl, and acid addition salts thereof.

2. The compound in accordance with claim 1, 10-(1-piperazinyl)-4H-thieno[3,4-b] [1,5]benzodiazepine.

3. The compound in accordance with claim 1, 10-(4-methyl-1-piperazinyl)-4H-thieno[3,4-b] [1,5]benzodiazepine.

4. The compound in accordance with claim 1, 4-methyl-10-(4-methyl-1-piperazinyl)-4H-thieno[3,4-b] [1,5]benzodiazepine.

5. The compound in accordance with claim 1, 7-chloro-10-(4-methyl-1-piperazinyl)-4H-thieno[3,4-b] [1,5]benzodiazepine.

6. The compound in accordance with claim 1, 6-chloro-10-(4-methyl-1-piperazinyl)-4H-thieno[3,4-b] [1,5]benzodiazepine.

7. The compound in accordance with claim 1, 7-chloro-4-methyl-10-(4-methyl-1-piperazinyl)-4H-thieno[3,4-b] [1,5]benzodiazepine.

8. The compound in accordance with claim 1, 10-piperidino-4H-thieno[3,4-b] [1,5]benzodiazepine.

* * * * *